United States Patent
Morrise et al.

(10) Patent No.: US 11,344,281 B2
(45) Date of Patent: May 31, 2022

(54) ULTRASOUND VISUAL PROTOCOLS

(71) Applicant: yoR Labs, Inc., Portland, OR (US)

(72) Inventors: Matthew C. Morrise, Portland, OR (US); Oliver C. Johnson-Terleski, Tualatin, OR (US)

(73) Assignee: YOR LABS, INC., Beaverton, OR (US)

( * ) Notice: Subject to any disclaimer, the term of this patent is extended or adjusted under 35 U.S.C. 154(b) by 0 days.

(21) Appl. No.: 17/445,680

(22) Filed: Aug. 23, 2021

(65) Prior Publication Data
US 2022/0061812 A1    Mar. 3, 2022

Related U.S. Application Data

(60) Provisional application No. 63/070,202, filed on Aug. 25, 2020.

(51) Int. Cl.
*G06F 3/048*    (2013.01)
*A61B 8/00*    (2006.01)
(Continued)

(52) U.S. Cl.
CPC .............. *A61B 8/465* (2013.01); *A61B 8/467* (2013.01); *A61B 8/5223* (2013.01); *A61B 8/54* (2013.01); *G06F 3/0481* (2013.01); *G06F 3/0488* (2013.01); *G06F 3/04845* (2013.01); *G16H 30/20* (2018.01); *G16H 30/40* (2018.01);
(Continued)

(58) Field of Classification Search
CPC ........ G16H 30/20; G16H 30/40; G16H 70/20; A61B 8/467; A61B 8/5223; A61B 8/54; G06F 3/0481; G06F 3/04845; G06F 3/0488
See application file for complete search history.

(56) References Cited

U.S. PATENT DOCUMENTS 5,617,371 A    4/1997    Williams
5,903,516 A    5/1999    Greenleaf et al.
(Continued)

OTHER PUBLICATIONS

Bradley, Aug. 2008, Retrospective transmit beamformation: Acuson SC2000 volume imaging ultrasound system, Siemens Medical Solutions USA, Inc., whitepaper, 8 pp.

*Primary Examiner* — David Phantana-angkool
(74) *Attorney, Agent, or Firm* — Knobbe, Martens, Olson & Bear LLP

(57) ABSTRACT

Systems and methods for performing ultrasound visual protocols to increase the speed and accuracy of examinations. A system can include an ultrasound probe, a storage medium for storing ultrasound visual protocols associated with anatomy to be examined, a storage medium on which a scan map comprising a graphical representation of anatomy being examined for a visual protocol is stored, and a touch-screen image display for displaying on a user interface scan map and visual protocol information, a working ultrasonic image of the anatomy being examined, and selectable thumbnail ultrasound images of the anatomy being examined. The display is responsive to receive, for an object identified in an image, object measurement and location information for a visual protocol, and in response to receiving the such information, to display visual protocol steps, location information of the object on the working image, and measurement information of the object.

19 Claims, 6 Drawing Sheets

Visual Protocol UI Representation

(51) Int. Cl.
*G16H 30/20* (2018.01)
*G16H 30/40* (2018.01)
*G16H 70/20* (2018.01)
*G06F 3/0481* (2022.01)
*G06F 3/04845* (2022.01)
*A61B 8/08* (2006.01)
*G06F 3/0488* (2022.01)
*G16H 40/67* (2018.01)
*G16H 15/00* (2018.01)

(52) U.S. Cl.
CPC ............ *G16H 70/20* (2018.01); *G16H 15/00* (2018.01); *G16H 40/67* (2018.01)

(56) References Cited

U.S. PATENT DOCUMENTS

| | | |
|---|---|---|
| 6,063,030 A | 5/2000 | Vara et al. |
| 6,120,450 A | 9/2000 | Li |
| 6,607,489 B2 | 8/2003 | Hoctor |
| 7,423,578 B1 | 9/2008 | Tietjen |
| 7,667,639 B2 | 2/2010 | Cheng et al. |
| 7,750,849 B2 | 7/2010 | Hjelmstad |
| 8,517,946 B2 | 8/2013 | Kim |
| 9,030,354 B2 | 5/2015 | Natarajan |
| 9,132,913 B1 | 9/2015 | Shapiro et al. |
| 9,323,445 B2 | 4/2016 | Kritt et al. |
| 9,342,156 B2 | 5/2016 | Huh |
| 9,986,969 B2 | 6/2018 | Call et al. |
| 10,401,492 B2 | 9/2019 | Brooks |
| 10,537,307 B2 * | 1/2020 | Yang ............... G06F 3/04842 |
| 10,624,612 B2 | 4/2020 | Sumi |
| 2002/0173721 A1 | 11/2002 | Grunwald |
| 2002/0173722 A1 | 11/2002 | Hoctor et al. |
| 2003/0055334 A1 | 3/2003 | Steinbacher et al. |
| 2004/0102700 A1 | 5/2004 | Asafusa |
| 2007/0200760 A1 | 8/2007 | Hjelmstad |
| 2007/0239001 A1 | 10/2007 | Mehi et al. |
| 2007/0259158 A1 | 11/2007 | Friedman et al. |
| 2008/0012753 A1 | 1/2008 | Cheng |
| 2008/0114239 A1 | 5/2008 | Randall et al. |
| 2008/0306385 A1 | 12/2008 | Jago |
| 2010/0030076 A1 | 2/2010 | Vortman et al. |
| 2010/0160784 A1 | 6/2010 | Poland |
| 2010/0251823 A1 | 10/2010 | Adachi |
| 2011/0077524 A1 | 3/2011 | Oshiki et al. |
| 2011/0137132 A1 * | 6/2011 | Gustafson ............ A61B 5/4312 600/300 |
| 2011/0208052 A1 | 8/2011 | Entrekin |
| 2012/0157851 A1 | 6/2012 | Zwirn |
| 2013/0227052 A1 | 8/2013 | Wenzel |
| 2013/0234891 A1 | 9/2013 | Natarajan et al. |
| 2013/0253317 A1 | 9/2013 | Gauthier |
| 2014/0035916 A1 | 2/2014 | Murphy |
| 2014/0046188 A1 | 2/2014 | Yen et al. |
| 2014/0058266 A1 | 2/2014 | Call et al. |
| 2014/0164965 A1 | 6/2014 | Lee et al. |
| 2014/0189560 A1 * | 7/2014 | Caspi ..................... G16H 40/63 715/771 |
| 2014/0219059 A1 | 8/2014 | Younghouse |
| 2015/0293223 A1 | 10/2015 | Park et al. |
| 2016/0161589 A1 | 6/2016 | Benattar |
| 2016/0161594 A1 | 6/2016 | Benattar |
| 2016/0161595 A1 | 6/2016 | Benattar |
| 2016/0165338 A1 | 6/2016 | Benattar |
| 2016/0165341 A1 | 6/2016 | Benattar |
| 2017/0090571 A1 | 3/2017 | Bjaerum |
| 2017/0307755 A1 | 10/2017 | Brooks |
| 2017/0343668 A1 | 11/2017 | Brooks et al. |
| 2018/0000453 A1 * | 1/2018 | Hunter ................ G06F 3/04883 |
| 2018/0055483 A1 | 3/2018 | Hunter |
| 2019/0324139 A1 | 10/2019 | Brooks |
| 2019/0353975 A1 | 11/2019 | DiDomenico |
| 2020/0170662 A1 * | 6/2020 | Vardi ............ A61B 17/320016 |
| 2020/0205783 A1 * | 7/2020 | Shiran .................... A61B 8/463 |
| 2020/0268351 A1 * | 8/2020 | Chiang .................. A61B 8/463 |
| 2021/0401508 A1 * | 12/2021 | Zhao ..................... A61B 34/10 |

* cited by examiner

*Visual Protocol UI Representation*

ULTRASOUND VISUAL PROTOCOLS

BACKGROUND OF THE INVENTION

Field

This disclosure relates to performing a visual protocol using ultrasound images. Specifically, this disclosure relates to associating protocol steps with a displayed graphical representation of a scanned body part, automatically displaying ultrasound images associated based on the protocol, and populating the protocol with annotations and other information to generate the visual protocol.

Description of the Related Art

Ultrasound imaging is used in the diagnosis, screening, and treatment of a variety of diseases and conditions. An ultrasound image is created by transmitting sound waves into the body and then interpreting the intensity of the reflected echoes. The echoes are commonly used to produce two dimensional, three-dimensional, and color flow images of internal anatomical features of patients. Ultrasound protocols are typically implemented as a simple checklist, for example, that is printed out and filled in during the examination. A practitioner uses the protocol as a guide for performing an ultrasound examination of a particular body part of the patient. Various examples of protocols may include instructions for capturing certain images of a body part (e.g., entire length of the body part, a transverse image, a side aspect image, a front aspect image, and the like), the type of image(s) to be collected (e.g., cine or still images), and measurements to be made of objects in the images. The ultrasound protocols may require certain annotations be made to indicate locations and/or other information of lesions and other objects depicted in the images. The information may include measurements, icons, labels, and observations of identified objects. The finished protocol allows the images and the ultrasound exam information to be used by another medical practitioner for subsequent diagnostics of the patient or other medical procedures such as surgery.

However, reviewing a completed ultrasound protocol can be complex and time-consuming because the ultrasound images, and the information determined in generating the ultrasound protocol, are not closely coupled together in an easily reviewable format or report. As the results of the ultrasound protocol are often reviewed by medical practitioners of different experience levels, and having expertise in different medical subject matter, use of the ultrasound protocol information may be inefficient to any particular user. Also, the current checklist requirements of ultrasound protocols may be interpreted differently by practitioners, such that the collected information may be different depending on the practitioner performing the protocol. Accordingly, it is desirable to have a more structured visual protocol procedure to improve the accuracy and speed and accuracy with which the ultrasound protocol is performed, and that closely associates collected images with determined examination information and annotations, and more strictly controls the images and information that is to ensure that it meets the needs of downstream medical practitioners.

SUMMARY

Provided herein is a system and method for performing a visual ultrasound protocol using active ultrasound scans (images), or previously stored ultrasound images. Visual protocols associate a protocol "checklist" or steps with a diagram of the scanned body part called a scan map and a series of thumbnail images called a gallery displayed concurrently with full size ultrasound images. The scan map contains location markers for each scanned image. Markers are automatically placed using IMU information from the ultrasound scanner and can be moved by the user. Each item in the checklist has a series of thumbnail images below it. There is also a text box for written description of images. These four elements (check list, scan map, text box and gallery) are cross referenced so that selecting an image/marker in one of three selects it on the other three and displays the full size image. Items that have a one to many mapping (e.g. scan map location markers or protocol steps) cycle through all associated images.

In one innovation, an ultrasonic imaging system for performing ultrasound visual protocols includes a processor; a storage medium, coupled to the processor, on which an ultrasound visual protocol is stored, the visual protocol having protocol steps indicating images and information to be collected to perform the visual protocol; a storage medium on which a scan map comprising a graphical representation of anatomy being examined for the visual protocol is stored, the scan map associated with the visual protocol; a touch-screen image display, coupled to the image processor and to the storage medium, the image display having a graphical user interface that shows, the visual protocol and the associated scan map, and information associated with steps of the visual protocol is displayed in a user interface, on a first panel of the display, an ultrasonic image of anatomy being examined with the selected visual protocol, and selectable thumbnail ultrasound images of the anatomy being examined, wherein the touch-screen display is responsive to receive for an object identified in an image, object measurement information and object location information based on the selected visual protocol, and in response to receiving the object measurement and location information, to display location information of the object on the image in the second panel and measurement information of the object in the first panel.

Various embodiments of such systems can have more or fewer features. For example, in some embodiments, the graphical user interface is generated and displayed to show the visual protocol and the associated scan map, and information associated with steps of the visual protocol is displayed in a user interface, on a first panel, an ultrasonic image of anatomy being examined with the selected visual protocol in a second panel, and selectable thumbnail ultrasound images of the anatomy being examined in a third panel. In some embodiments, the system also includes an ultrasound probe in communication with the processor for acquiring ultrasonic images. In some embodiments, the user interface is configured to receive a selection of an ultrasound visual protocol, and in response to display steps for the selected ultrasound visual protocol. In some embodiments, the user interface is configured to receive a selection of a step of the selected ultrasound visual protocol, and in response to display a scan map associated with the selected step of the ultrasound visual protocol. In some embodiments, for a selected step, the user interface is configured to receive a selection of an ultrasound image, and wherein the system is configured to associate the selected ultrasound image with the selected step, to save the image, and to add a thumbnail image of the selected ultrasound image on the user interface, the thumbnail image having an indicator showing it is the selected image. In some embodiments, the user interface is configured to receive input to add a scanned position of the selected image to the scan map. In some embodiments, the user interface is configured to display information needed to be determined based on the selected protocol, and to receive touch inputs to measure an object displayed on the working image, and wherein the system is configured to determine measurements of the object and display them in the first panel of the user interface. In some embodiments, determined measurements comprise the area of an object. In some embodiments, the determined measurements comprise the perimeter of an object.

Another innovation is a method of performing a visual ultrasound protocol, the method can include generating and displaying on a touch-screen image display, a graphical user interface that to display information and receive input for performing a visual protocol. The method of generating and displaying the graphical user interface can include displaying one or more visual protocols, in response to receiving an input selection of a visual displayed protocol to perform, displaying steps of the visual protocol on the graphical user interface. For each step in the protocol, in response to receiving an input selection of a protocol step, automatically displaying an associated scan map, and in response to receiving an input selection of a displayed image to save, generating thumbnail representation of the image and display the thumbnail representation in a panel on the graphical user interface for displaying the gallery of thumbnail image representations, displaying the thumbnail representation in the protocol step, associating the image with a scan location on the scan map, and displaying the scan location on the scan map. The method can also include, in response to receiving measurement information relating to the image, associating the measurement information with the image and the protocol step. The method can also include, in response receiving annotation information relating to the image, associating the annotation information with the image and the protocol step, and storing the visual protocol such that the stored visual protocol includes associations to all of the images, measurements, and annotations related to each of the steps of the visual protocol.

Another innovation includes a system for performing visual protocols by displaying ultrasound images and corresponding visual protocols, including images rendered from the ultrasound image and measurements and location information of objects in the ultrasound images, the system comprising a processor and a storage medium coupled to the processor. The storage medium stores computer-executable instructions, an ultrasound visual protocol, the visual protocol having protocol steps indicating images and information to be collected to perform the visual protocol, and a scan map associated with the visual protocol, the scan map comprising a graphical representation of anatomy being examined for the visual protocol. the system also includes one or more computer hardware processors in communication with the at least one non-transitory computer storage medium, the one or more computer hardware processors configured to execute the computer-executable instructions to: display one or more visual protocols, in response to receiving an input selection of a visual displayed protocol to perform, display steps of the visual protocol on the graphical user interface, for each step in the protocol, in response to receiving an input selection of a protocol step, automatically display an associated scan map, in response to receiving an input selection of a displayed image to save, generate thumbnail representation of the image and display the thumbnail representation in a panel on the graphical user interface for displaying the gallery of thumbnail image representations, display the thumbnail representation in the protocol step, associate the image with a scan location on the scan map and display the scan location on the scan map, in response to receiving measurement information relating to the image, associate the measurement information with the image and the protocol step, in response receiving annotation information relating to the image, associate the annotation information with the image and the protocol step, and store the visual protocol such that the stored visual protocol includes associations to all of the images, measurements, and annotations related to each of the steps of the visual protocol.

Another innovation includes an ultrasonic imaging system for performing visual protocols by displaying ultrasound images and corresponding visual protocols, including images rendered from the ultrasound image and measurements and location information of objects in the ultrasound images, the system comprising: one or more computer hardware processors; a storage medium storing computer-executable instructions, an ultrasound visual protocol, the visual protocol having protocol steps indicating images and information to be collected to perform the visual protocol, and a scan map associated with the visual protocol, the scan map comprising a graphical representation of anatomy being examined for the visual protocol. The one or more computer hardware processors are in communication with the at least one non-transitory computer storage medium, and the one or more computer hardware processors are configured to execute the computer-executable instructions to: generate and display in a user interface a first panel including the visual protocol and the associated scan map, and information associated with steps of the visual protocol; generate and display in the user interface a second panel including an ultrasonic image of anatomy being examined with the selected visual protocol; generate and display in the user interface a third panel including selectable thumbnail ultrasound images of the anatomy being examined; and receive wherein the touch-screen display is responsive to receive for an object identified in an image, object measurement information and object location information based on the selected visual protocol, and in response to receiving the object measurement and location information, to display location information of the object on the image in the second panel and measurement information of the object in the first panel.

DETAILED DESCRIPTION

Overview

Figure 1:
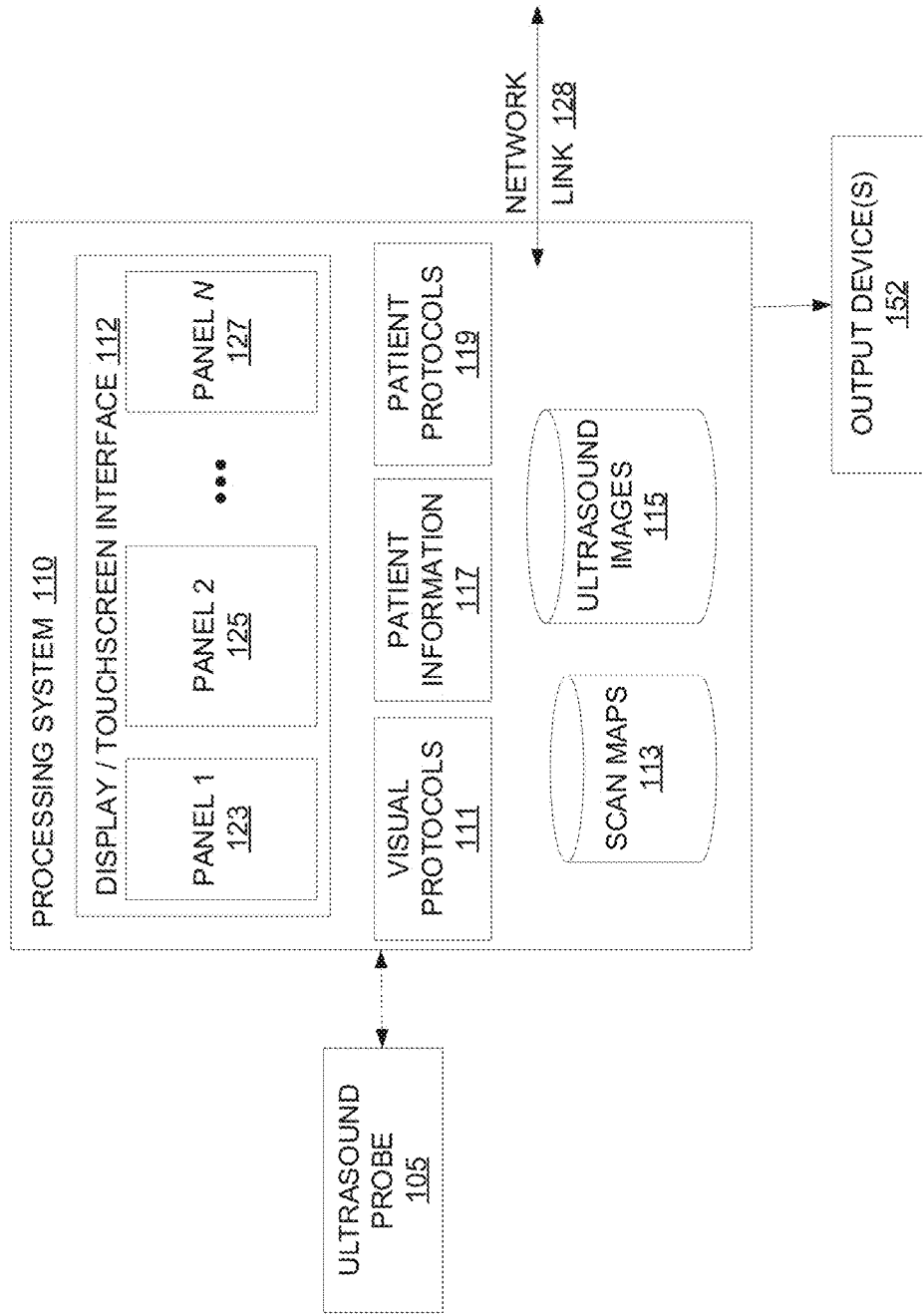
FIG. 1 is a block diagram illustrating an example of an ultrasound system.

Embodiments of systems and methods for performing visual ultrasound protocols are disclosed herein. A software application provides a user interface for selecting, visualizing, and interacting with visual ultrasound protocols, including ultrasound image association, annotation and measurement of objects in an ultrasound image, including suspect objects and a patient's anatomy in an image. For example, a method may include selecting a protocol, from a list display protocols, to perform for patient. The method may also include selecting a protocol step, saving captured ultrasound images of interest in associating them with a protocol step, adding information (e.g., a scan position) to a scan map that depicts a graphical representation of the scanned anatomy, and adding annotations and/or measurements to the protocol.

Each protocol step may be linked to ultrasound images and other information relating to the protocol step, such that when the protocol step later is selected, the linked ultrasound images and information are displayed and available to the operator. The system can guide the ultrasound operator through the steps of the protocol and ensure that all the requirements of the protocol have been met before the protocol is marked as completed. Once a protocol has been completed, the information and images associated with the protocol may be printed as a report, communicated to another medical practitioner for examination/review, or stored for later use.

Terms

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

"Database" in this context refers to an organized collection of data (states of matter representing values, symbols, or control signals to device logic), structured typically into tables that comprise 'rows' and 'columns.'

"Final Report" in this context refers to the final product of an ultrasound scan including written documentation of the imaging findings and an impression or diagnosis based on those findings.

"Graphical representation" in this context refers to a stylized drawing of the body part being scanned.

A "loop", "cineloop", "time-lapse", or "video loop" in this context may be used interchangeably to refer to a time series of images. In some embodiments, a 4D image may be a time-lapse of 3D image(s). In other embodiments, individual frames can be sequenced to form a video loop.

"Module" in this context refers to logic having boundaries defined by function or subroutine calls, branch points, application program interfaces, or other technologies that provide for the partitioning or modularization of particular processing or control functions. Modules are typically combined via their interfaces with other modules to carry out a machine process.

"Protocol" in this context refers to a written outline, checklist, or worksheet that list images and measurements that should be acquired during the specified ultrasound examination.

"Reader" in this context refers to the person interpreting the ultrasound scan.

A "scanner" or "ultrasound device" in this context refers to a device for performing ultrasound imaging (sonography), which uses high-frequency sound waves to examine an object. The device may comprise an ultrasonic transducer or an ultrasonic transducer array used to probe the object. Transducers may be part of a sequential array in which the acoustic beam is focused straight in front of the transducer, providing high sensitivity but a limited field of view, or a phased array in which each transducer sends an acoustic beam in a coordinated sequence, establishing a pattern of constructive interference that results in a beam at a set angle, allowing for a wider field of view. Phased array transducers may comprise multiple transducer elements which may be arranged in a variety of shapes including a strip (linear array), a ring (annular array), a circular matrix (circular array), conformal array, curved, or a more complex shape. A "scanner" used herein may be hand-held or portable.

"Ultrasound study" in this context refers to a diagnostic procedure performed by a sonographer that uses two-dimensional images produced by inaudible sound waves to evaluate an anatomical feature.

"User" in this context refers to the person performing an ultrasound scan. "Reader" in this context refers to the person interpreting an ultrasound scan. A "sonographer" may both perform and interpret an ultrasound scan.

"Scan plane" in this context refers to the orientation of the ultrasound probe relative to the part being scanned.

When 3D imaging is available, ultrasound viewing and saving may include three modes: scanning, frozen, and review. "Scanning" in this context refers to showing images directly from the scanner (e.g., the ultrasound device). "Frozen" in this context refers to showing the last N seconds of images from the scanner. "Review" in this context refers to showing images that are explicitly saved.

A "frame" in this context is for specifying the space and time aspect of an image. In other words, a frame is the image at a given position with respect to the time the image was taken. In some embodiments, a "frame" may be a 2D image. In other embodiments, when a user is performing the 3D imaging mode via an ultrasound device, a "frame" may additionally cover each image taken by the ultrasound device in that same instance.

"Scan plane" in this context refers to the orientation of the ultrasound probe relative to the part being scanned.

"Structured labels" in this context refers to a list of labels used for a specific exam type in which the labels are automatically presented in a set order.

"Slices": Bundled images in frozen and review modes are called a "capture" and there are four types of capture: 2D image, 2D series (cineloop), 3D image, and 3D series (3D cineloop). The information (or image data) that constitute ultrasound 3D image captures are called "slices". A "slice" in this context may be a thin 3D composite image formed from a collection of 2D images.

A "thick slice mode" in this context refers to a 3D image taken by an ultrasonic transducer array. A "tomography" in this context refers to a time series of 2D or 3D images taken by an ultrasonic transducer array is in motion relative to the object being scanned.

"Touch screen" in this context refers to a capacitive or resistive display which responds to direct touch manipulation, either by finger (simple or multi-touch), stylus, or both. The user can use the touch-screen to react to what is displayed and to control how it is displayed. The touch-screen enables the user to interact directly with information displayed rather than using a mouse, touchpad, or other intermediate device (with the exception of a stylus).

"Ultrasound study" in this context refers to a diagnostic procedure performed by a sonographer that uses two-dimensional images produced by inaudible sound waves to evaluate an anatomical feature.

"User" in this context refers to the person actually performing the ultrasound scan.

"Visual Protocol" in this context refers to a protocol that is displayed on a display screen of a computer system, and that is updated based on a user's interactions. The visual protocol can associate a protocol checklist with a diagram of a scan map (a diagram of the scanned body part). The visual protocol can also associate the protocol checklist with a textual list of annotations for the image and a series of thumbnail images (a "gallery"), where each of the thumbnail images is associated with a full-size ultrasound image that can be when the thumbnail image is selected. The visual protocol can also associate the protocol checklist with measurements that are to be acquired during the specified ultrasound examination.

"Word bank" in this context refers to a list of context-specific labels which are commonly used for a specific scan type or body part.

"Worksheet" in this context refers to a generated document comprising patient information, scan information, and images and written findings from the ultrasound.

Data Representation

In some embodiments, the data representation of a scanned image may be able to represent all the needed fields to both display and to signify the exact display variant the renderer should use. Additionally, the data format may be flexible enough to allow for transformations to other supported display variants if possible.

The data implementation may represent a single slice or a single frame, or captures which are collections of images along with other properties. Checking the contents of captures allows for explicitly knowing the type of scan and variant needed to display. Knowing this type then specifies all actions that can be taken on the capture, as well as directing the display renderer how it should render the image data.

An image may be a single frame or a single slice. In some embodiments, image data that is saved to the database for an individual image may include the following immutable fields:

(1) Raw pixel data for what was imaged.
(2) Depth details to specify constraint of bottom of image. The depth refers to a 2D image's y-axis which corresponds to how deep the scanner is imaging.
(3) Timestamp to have relative timing information relative to other image data
(4) Relative position data in x, y, and z directions.
(5) Relative angle position data in x, y, and z directions.
(6) Relative slice position and total number of slices for beamformed 3D image if applicable.

Bundled images in frozen and review modes are called a capture. A capture may be a 2D image, a 2D series (cineloop), a 3D image, or a 3D series (3D cineloop). A capture may include multiple frames and/or slices, where the multiple frames may include images that are changing in time, and multiple slices may include images that are changing spatially. A capture may be the full collection of the images taken over both time and space. Different capture types represent different display variants, including:

(1) A "frame", which is a single image at a given time point.
(2) A "loop", which include multiple images focused on essentially the same spatial area but changing in time.
(3) A "slice", which includes images of a spatial range near a spatial position. Multiple slices are used to create a 3D image.
(4) A "2D time-lapse" or a 3D "time-lapse", which includes images taken in the same location over a time range.
(5) A "thick slice", which includes images taken in 3D mode in a stable location with a given spatial and time sampling rate.
(6) A "tomography", which includes images taken while traversing (moving the scanning probe) a region that is both time and spatially variant.
(7) A "loop", which is a time series of data. The spatial information can be rendered in 3D or as a 2D plane. As each image data has time and spatial information, projections between the different dimensions can be made.

Example Visual Protocol System

FIG. 1 is a block diagram illustrating an example of an ultrasound system 10 for completing a visual protocol. The ultrasound system 10 includes an ultrasound probe 105 that communicates with a processing system 110. The ultrasound probe 105 can be a handheld ultrasound device that comprises a transducer array configured to transmit an ultrasound signal to a target object, receive an ultrasound echo signal reflected from the target object, and form ultrasound data corresponding to the target object. The processing system 110 can be any type of computer device (e.g., a desktop computer, a tablet, a laptop, or another mobile device) that is suitably configured to perform visual protocols. The ultrasound probe 105 can be controlled by the processing system 110 to provide ultrasound images to the processing system 110.

The processing system 110 can include a display/touch-screen interface 112 ("interface") that can display a visual protocol, ultrasound images, measurement information and other information related to the visual protocol in one or more panels 123, 125, and 127. In some preferred embodiments, the display screen and the user interface are implemented together such that most, or all, of the controls to complete the visual protocol are available on the interface 112, but some systems may have a separate display and interface. The interface can be any type of a flat screen, LED screen, electroluminescent display, organic LED, LCD, virtual display and the like that can display information and receive input from a user in the directly to the display or to another device that is in communication with the display. The processing system 110 may also include voice recognition to manipulate information and/or images on the interface 112.

The interface 112 may present information in a variety of ways. In some embodiments, the interface 112 is divided into a plurality of panels (or sectors) 123, 125, and 127 in any order, each of which may contain one or more of: a visual protocol, patient information, an active ultrasound image being currently acquired from a machine transformation of an ultrasound reading in process (active scan), thumbnails of ultrasound images from the current exam, and thumbnails of recorded images from a previous exam. In some embodiments, the thumbnails may be presented in chronological order. In other embodiments, the thumbnails may be presented in an order chosen by the user. Each thumbnail image may be expanded, moved, or removed as desired using gestures on the user interface. In some embodiments, the thumbnails may be stacked one on top of each other with the most recent scan on top. In other embodiments, thumbnails may be presented in discrete rows. Thumbnails may be labeled with the date and time of the scan as well as any other relevant label or descriptive information including, but not limited to, patient information, scan location, scan date, scan plane, anatomical subject of the scan, presence or absence of lesions, purpose of the scan, measurements of lesions, number of lesions and the like. As described in more detail in reference to FIG. 3, the interface 112 can display information related to the visual protocol being performed (e.g., protocol steps) and receive user input via its touchscreen functionality, or other input devices (e.g., keyboard, mouse, and the like) that are in communication with the processing system 110.

Performing the visual protocol may generally include, for example, selecting a visual protocol to perform, associating the visual protocol and the ultrasound images with a patient, and receiving ultrasound images from the ultrasound probe 105. Performing the visual protocol may also include recording, associating, measuring comparing, labeling, reporting and/or documenting information received from an ultrasound probe. The plurality of panels 123, 125, and 127 on the interface 112 allow for the display of the visual protocol, interaction with one or more ultrasound images and graphical representations, and measurement of objects depicted in ultrasound images. The processing system 110 may include various modules to facilitate the completion of the visual protocol for example, the processing system 10 may include a measurement module activated by the user interface to determine appropriate measurements of portions of a displayed ultrasound image (e.g., of an objected visible in an ultrasound image) and to a graphical representation of the measurement on a target object. The processing system 110 may also include a labeling module activated by the user interface to add the appropriate labels to the active ultrasound image and to a graphical representation of the target object. The processing system 110 may include a computer visualization application operated via the user interface for the display of the visual protocol, ultrasound images associated with the visual protocol, and measurements and labels associated with the visual protocol.

The processing system 110 may store information that is used to perform the visual protocol. For example, the processing system 110 may store one or more of visual protocols 111, patient information 117, scan maps 113, ultrasound images 115 (e.g., that are either generated during the exam or are from previous exams), and completed patient protocols 119. In some embodiments, one or more of the visual protocols, scan maps, patient information, ultrasound images, and completed patient protocols are stored on a system that is in communication with the processing system 110 via a network link 128. For example, because of the potentially large size of the images that may be collected while performing a visual protocol, at least some of the ultrasound images that are collected may be stored on a high-speed computer storage device is in communication with the processing system 110 via the network link 128. The processing system 110 may also include one or more output devices 152 that can be used to, for example, generate a report or provide the visual protocol "package" having information and images that is stored and subsequently used for further analysis of a patient.

The visual protocols 111 include information that is required to complete a particular visual protocol. For example, a list of steps to complete, images of certain anatomy that are needed, measurements that are needed, and criteria (e.g., size) relating to objects in the ultrasound images that indicate that additional information images or steps are needed if the objects meet the particular criteria. Steps of a visual protocol can be displayed on the interface 112, a step can be selected, and information (e.g., images, measurements, annotations) needed to complete the step is displayed. A user can then quickly and efficiently provide input to the interface 112 to display and indicate to associate one or more images with the step, perform measurements required for the step, and provide annotations as required by each step of the visual protocol. The processing system 110 associates the indicated images, measurements and annotations automatically and generates a completed visual protocol package when all the steps of been completed, for the examinations complete.

As mentioned above, the interface 112 may be a combination display and touch screen that allows the user to manipulate the images on the display. Touch-screen based computers comprise computer assemblies combining an internal computer processor and touch sensitive digital display screen. The display and the computer's ability to monitor the positions and motions of finger touches on the touch-screen are coordinated such that finger contact locations can be correlated by the computer with the information displayed at those locations. A variety of gestures may be used to interact with the interface 112, including, but not limited to, touching, swiping, double tap, multiple finger taps, pinch, multi-touch, radio buttons and the like. A processor is coupled to the touch-screen for detecting a touch by the user on the touch-screen that identifies a selected activation area. The processor then performs the device function associated with the stored image manipulation function thereby activating the selected activation area. In some embodiments, the user may interact with the interface 112 through voice recognition, a stylus, keyboard, mouse, virtual reality headset, hand gestures in the air, any other way generally used to interact with a user interface, or a combination thereof. In some embodiments, controls on the ultrasound probe 105 may be used to input information onto either or both the interface 112.

The interface 112 can be divided into a plurality of control panels including, but not limited to, a proportionate graphical representation of the anatomical part being scanned, a scale or other measuring apparatus, a track pad, a series of one or more virtual controls such as buttons or radio buttons, word bank, structured label bank, tabbed drop down menus, virtual keyboard, active ultrasound image, virtual trackpad, virtual depth and focus sliders, virtual cine slider, and virtual time gain compensation sliders. In some embodiments, the number and arrangement of control panels may be altered to suit the needs of the user. For example, during a scan, it may be desirable to have an extended display of one or more of the control panels. In some embodiments, there may be one control panels. In other embodiments, there may be 2, 3, 4, 5, 6, 7, 8, 9, 10, 11, 12 or more control panels. Activation of each panel on the interface 112 may perform a function on interface 112 and can manipulate information on the interface 112.

Patient Information and Protocols

In some embodiments, a visual protocol may be stored on the ultrasound system 10, input to the ultrasound system 10, or stored on another system that is in communication with the ultrasound system 10. Patient information may be input to a visual protocol, or associated with a visual protocol. For example, patient information may be input through the interface 112. In some embodiments, the visual protocol is associated with a patient identifier or patient information, and the protocol is populated automatically by the associated patient information. In some embodiments, patient information is previously stored (e.g., in a database) on the ultrasound system 10, or on another system that is in communication with the ultrasound system 10. For example, patient information, prior scans, protocols, and/or prior protocols may be retrievable from a network based database. For example, in a hospital or other examination facility, a network-attached server may store patient information, images and image acquisition settings such that they can be accessed from imaging devices in different locations. Once a protocol and/or patient information is inputted through the touch-screen display and the scan type is indicated, the visualization application on the touch-screen may populate the touch-screen with a graphical representation of the location of the anatomical scan, and populates one or more of the word bank, structured label bank, and drop down menus with context-specific labels pertinent to the anatomical location. If prior visual protocols (or regular written protocols) have been performed, the display may present a list of the prior protocols, and information associated with the prior protocols.

Labels and Annotations

Typically useful ultrasound images require at least two labels: the anatomical region being imaged and the scan plane or transducer orientation. Additional information that may be included with an image includes, but is not limited to, measurements of an anatomical feature of interest including the longest horizontal diameter, the anteroposterior diameter, and the orthogonal horizontal; the location of the anatomical feature of interest in reference to anatomical landmarks (such as the chest wall); the type of lesion or anatomical feature of interest; the orientation of the lesion of interest; the location and depth of the lesion of interest and the like.

An anatomical feature of interest may include in its label whether it is transverse (TR) or longitudinal (LG) indicating the direction of the scan; whether the lesion is a cyst, mass, duct or blood vessel; whether it is located anterior to or posterior to an anatomical landmark; its size and the like. For example, in a breast ultrasound, an anatomical feature of interest may include in its label whether it is the right or left breast, the clock face location in the breast, whether the scan plane is radial (RAD), anti-radial (AR-ARAD), transverse (TR), longitudinal (LG), and/or descriptive labels such as whether the lesion is a cyst, mass, duct or blood vessel, whether it is located anterior to or posterior to an anatomical landmark such as the nipple or chest wall, the measurements and number of lesions, and the like.

In some embodiments, a displayed list of structured labels, or a manual entry of a label may be used to add information to labels or to modify existing information on a label regarding the active scan. In some embodiments, labels for all body parts are listed. In some embodiments, where there are a finite number of anticipated or commonly used labels for a specific anatomical feature, the labels may be listed in a word bank. For example a word bank for a breast study may include, but is not limited to, RAD, ARAD, SAG, TRAN, Axilla, Axillary tail, Subareolar, Inframammary fold, Anterior Axillary line, Middle Axillary line, Posterior Axillary line, Palp, Palp area, Tract, Calcifications, Heel rock, Toe rock, Skin fascia, Chest wall, Lateral to, Medial to, Cyst, Foam cyst, FA, Mass, Halo, Typical, swirling echoes, and vessel. A word bank for a thyroid study may include, but is not limited to, Right, Left, SAG, TR, Isthmus, upper pole, mid gland, lower pole, Esophagus, Cyst, Cystic changes, Microcalcifications, Thyroid bed, and Lower pole obscured by clavicle. A word bank for a cervical node study may include, but is not limited to, Cyst, Cystic changes, Calcification, Microcalcifications, Hilar flow, Cortical flow, and Thyroid bed.

Structured labels may be used where a scan generally proceeds in a standard order and typical images are acquired. Standardized labels may appear in order and the user merely accepts the labels. Common scan types for structured labeling would include, but are not limited to, obstetrics, abdomen, carotid, lower extremity venous among others. The order and the labels in the structured label list may be fixed or customizable. In some embodiments, structured labels for an obstetric scan for maternal and fetal anatomy may be customized to be presented in the order the sonographer usually scans: for example, cervix, placenta trans, placenta long, ventricles, CSP, CM, orbits, face, N/L and profile, among others. For a thyroid study, the structured labels presented may include, but are not limited to, Right, RUP TR, R mid TR, RLP TR, R SAG lat, R SAG ML, R SAG med, R Level IV LN, Isthmus TR, Isthmus SAG, Left, LUP TR, L mid TR, LLP TR, L SAG med, L SAG ML, L SAG lat, and L Level IV LN. The structured labels for a cervical node study may include, but are not limited to, Right Neck with sub labels including Level I, TR; Level I, LG; Level IIA, TR; Level IIA, LG; Level IIB, TR; Level IIB, LG; Level III, TR; Level III, LG; Level IV, TR; Level IV, LG; Level V, TR; Level V, LG; Level VA, TR; Level VA, LG; Level VI TR; Level VI, LG; Thyroid bed, TR; and Thyroid bed, LG. The Left Neck may appear with sub labels including, but not limited to, Level I, TR; Level I, LG; Level IIA, TR; Level IIA, LG; Level IIB, TR; Level IIB, LG; Level III, TR; Level III, LG; Level IV, TR; Level IV, LG; Level V, TR; Level V, LG; Level VA, TR; Level VA, LG; Level VI TR; Level VI, LG; Thyroid bed, TR; and Thyroid bed, LG. Labels may also include numbers indicating the presence of a plurality of lesions and providing reference tags for follow up studies of each lesion. In some embodiments, each lesion may be numbered automatically.

Identification labeling of the scan image on the display may occur by interacting in one or more ways with the interface 112. For example, in some embodiments, placement of the identification labels may occur by tapping on the graphical representation on a panel of the interface 112 displaying a target object in an ultrasound image. When a location is tapped, a marker may appear on the graphical representation showing the location of the tap on the drawing and a location label corresponding to the marker may appear on the displayed active ultrasound image. The position of a label on the graphical representation may be re-positioned by selecting and dragging it. A directional swipe on the graphical representation may provide the scan plane label for the active image on the first display. If multiple lesions are being documented, the tap on the graphical representation may add a lesion number to the label on the active scan. In some embodiments, the same labels may appear on the graphical representation and the active scan when the graphical representation is manipulated. In other embodiments, different labels may appear on the graphical representation and the active scan. In further embodiments, some labels may appear on the graphical representation or the active scan, but not both. For example, transducer direction is necessary for the ultrasound image, but is less so for the graphical representation. In additional embodiments, a label placed on the active image may be copied on the matching location on the graphical representation. The annotated graphical representation may become part of a study and be used as a data summary and/or as part of a final report. In additional embodiments, indicating placement of a lesion on the graphical representation on the user interface will create a lesion number and will capture the measurements of the lesion. In some embodiments, the label may include one or more symbols indicating the type of lesion or anatomical part shown in the ultrasound. For example, there may be symbols for a mass, duct, vessel, cyst, malignancy, benign lesions, lymph nodes, and the like. Such symbols may be dragged, stretched, pinched, or otherwise manipulated to more closely resemble the placement, size and shape of the actual lesion.

Figure 2:
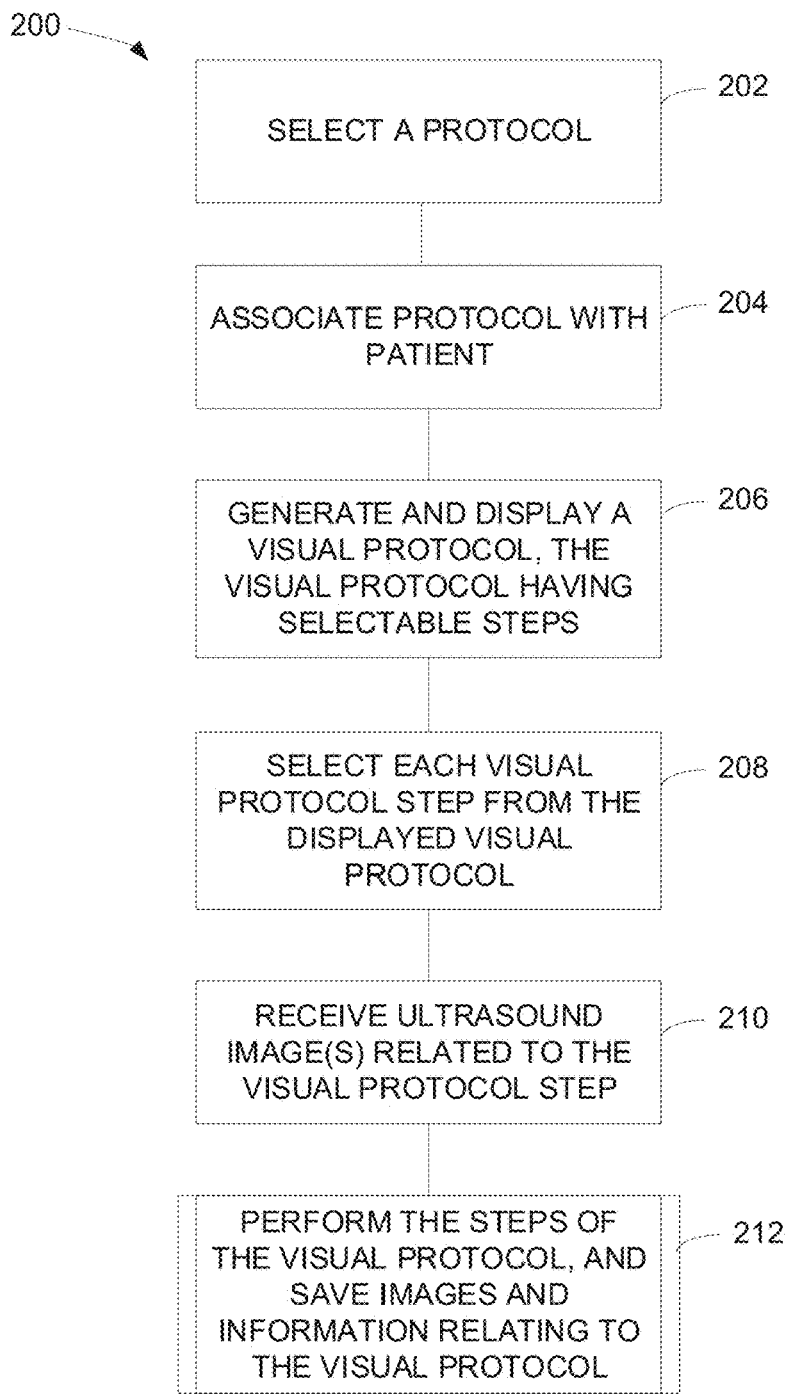
FIG. 2 is a flow chart that illustrates an example of a process for performing a visual protocol, which can be performed on the ultrasound system illustrated in FIG. 1.
Figure 3:
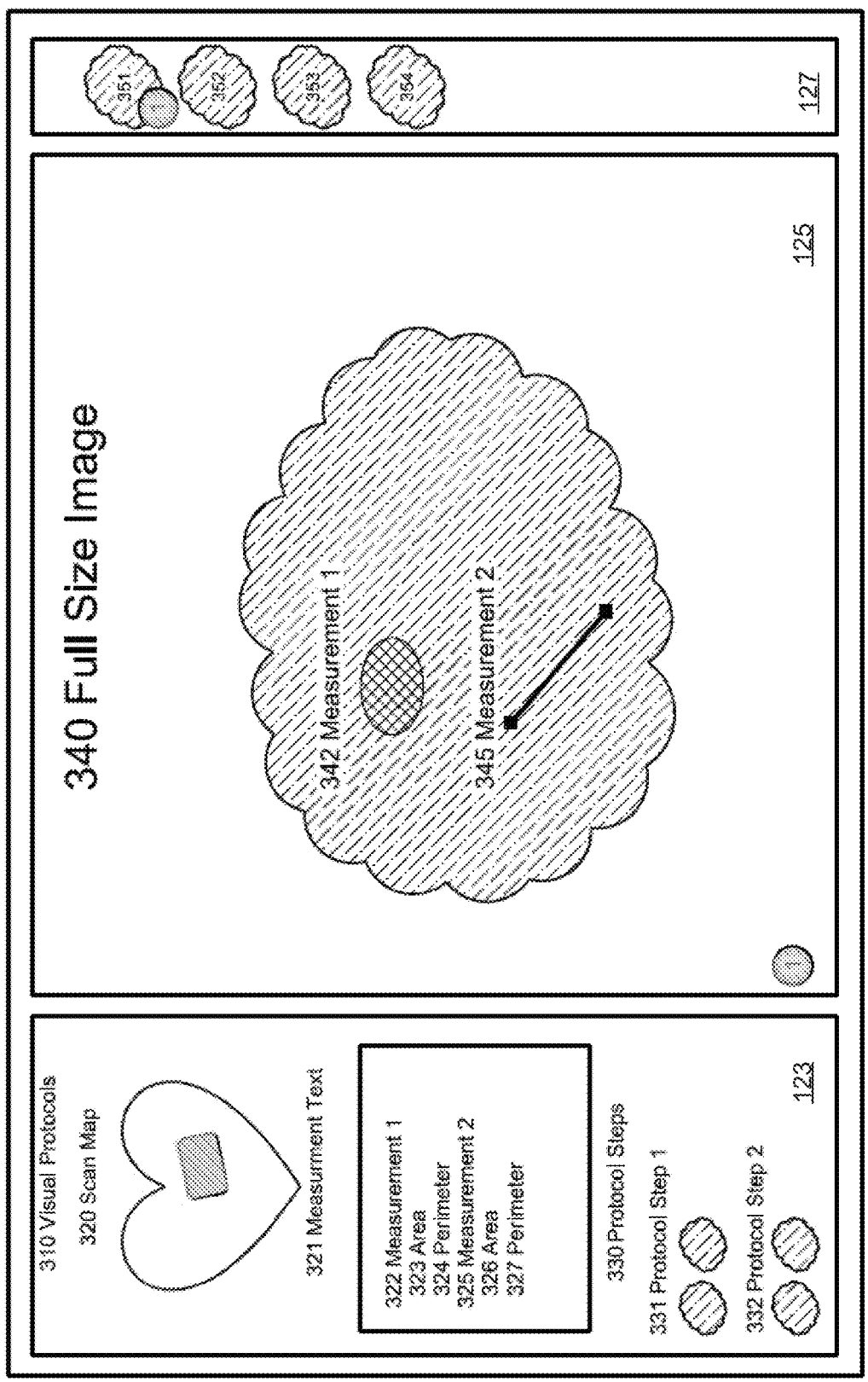
FIG. 3 is a diagram illustrating a graphical user interface (GUI) that can be generated on a touch screen display, the GUI having panels for displaying a visual protocol and ultrasound images, and the GUI also having selectable features that allow a user to input or generate information relating to measurements, annotations, and other information related to the patient, the protocol, or ultrasound images.

FIG. 2 is a flow chart that illustrates an example of a process 200 for performing a visual protocol. Process 200 can performed on the ultrasound system illustrated in FIG. 1, for example, using a graphical user interface (GUI) presented on a touchscreen display. As an example, FIG. 3 illustrates a GUI that can be generated and presented on the interface 112 and used to perform a visual protocol, displaying information and receiving inputs form a user to perform the visual protocol. In this example, GUI includes panels 123, 125, 127 that display visual protocol information and related ultrasound images. Specifically, in this example, a visual protocol 310 is displayed in panel 123. The visual protocol 310 may include a scan map 320, measurement information 321, and protocol steps 330. A relatively large ultrasound image 340 is displayed in panel 135, and is referred to as the "working image." The GUI can display the working image as a full size image, or the GUI can be employed to zoom in/out on the working image 340 based on the needs of the protocol. One or more graphics may be displayed on the working image 340 to facilitate completing the visual protocol. For example, a first measurement 342 and a second measurement 345. One or more thumbnail images may be displayed in third panel 127. Selection of any of the thumbnail images 351, 352, 353, 354 causes the selected thumbnail image to be displayed in the second panel 125. The thumbnail images may include an indicator (e.g., a "1") to show which of the thumbnail images is currently being displayed as the working image in the second panel 125. The GUI includes selectable features that allow a user to input or generate information relating to measurements, annotations, and other information related to the patient, the protocol, or ultrasound images.

At block 202 of the process 200 for performing a visual protocol, a desired visual protocol may be selected, e.g., from a list of possible visual protocols that can be performed that are accessible on the processing system 110. The list of possible visual protocols may be displayed at the start of the process, for example, in the first panel 123. The selected visual protocol is associated with the scan map that provides a graphical representation of the scanned body part that the visual protocol is being used to examine. When completed, the visual protocol is associated with the scan map, the ultrasound images, and a textual list of annotations relating to the visual protocol. When the visual protocol is displayed, the scan map, annotations, thumbnail images, and a selected larger (or full size) image of one of the thumbnail images can be displayed.

At block 204, the visual protocol is associated with a patient. This can be done, for example, by entering patient information indicating the patient associated with the visual protocol, from stored patient information 117, or patient information received via the network link, or manually entered by the user.

At block 206, the visual protocol is generated and displayed. The visual protocol includes selectable steps one or more of which are also displayed (e.g., Protocol Step 1 331, Protocol Step 2 332, etc.). To perform the visual protocol, at block 208, the user selects a protocol step and in response the system displays information related to the selected protocol step, for example, measurements and images related to the protocol step. The steps need not be selected in any particular order. Images captured while performing a selected step will be associated with that step of the visual protocol. Later if desired, an image may be unassociated with a previously associated step. Also, an image maybe associated with a different step as well.

At block 210, the system receives one or more ultrasound images for the selected protocol step. An image may be a new image received from the ultrasound probe 105, or the image may be a previously captured image. At block 212, the user performs the steps the visual protocol, associating one or more image with the step of the visual protocol and performing measurements and making annotations required for the visual protocol steps. Additional details of performing steps the visual protocol described below in reference to the flowchart illustrated in FIG. 4.

Figure 4:
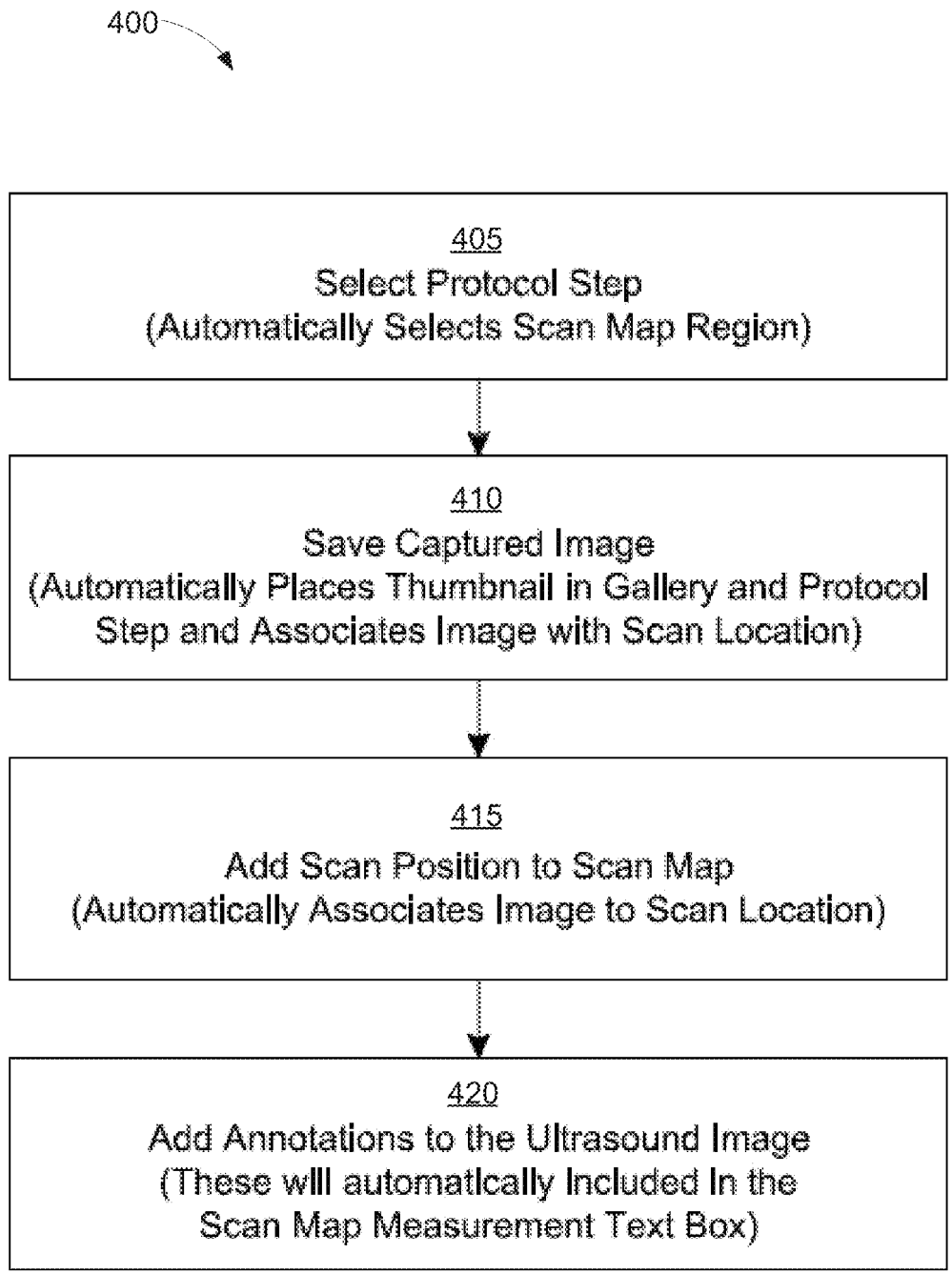
FIG. 4 is a flow chart that illustrates an example of a process for performing steps of a visual protocol, which can be performed on the ultrasound system illustrated in FIG. 1.

FIG. 4 is a flow chart that illustrates an example of a process 400 for performing steps of a visual protocol, which can be performed on the ultrasound system illustrated in FIG. 1. As shown in FIG. 3 and as mentioned above, a graphical user interface rendered on a touch screen displays the visual protocol, a scan map 320 (a graphical representation of the scanned body part), steps of the visual protocol 330, a textual list of annotations for a displayed working image, and a series of thumbnail images 351-354 called displayed concurrently with working ultrasound image. The visual protocol associates a protocol checklist with the scan map, the textual list of annotations and a series of images. As illustrated in FIG. 3. when displayed on a graphical user interface, each step in the visual protocol checklist has a series of thumbnail images below it. The scan map 320 contains location markers for scanned images. On the graphical user interface there is also a text box 1 for measurements of made on a working image. The visual protocol automatically associates all of the information and images that are related to each protocol step, greatly increasing the efficiency of performing the protocol. Also, because all the information and images are automatically associated with each other and with a respective protocol step, the generated visual protocol is highly organized is much more easily used for subsequent analysis of the results. Process 400 describes the example of steps for creating a visual protocol once a particular visual protocol has been selected to be performed.

At block 405, the user selects a protocol step from a list of protocol steps. Steps need not be selected in order. Once a protocol step is selected images, captured during that protocol step will be automatically associated with that step. An image that is associated with a protocol step can later be unassociated with that protocol step, or associated with a different step at a later time. When the protocol step is selected, the system automatically selects the region on the scan map that is associated with a protocol step.

At block 410, the user saves a captured image that is being displayed on the graphical user interface. The graphical user interface can include a control button that the user activates to save a displayed image. When images saved, the full size image is displayed on the graphical user interface, and the system associates the saved image with the currently selected protocol step in associates the image with the scan location. Also, the system adds a thumbnail of the image beneath the protocol step being performed and adds a thumbnail of the saved image to the gallery, and adds an indicator signifying that the thumbnail is the working image.

At block 415, the user adds the scanned position of the saved image to the scan map, and it may show up as a marker on the scan map. The scanned position can be moved and rotated after being added. The marker for the scanned position is automatically given a number, a color, and a tag with this number and color are added to the full size image. The number, color, and tag are also added to the corresponding image in the thumbnail in the gallery, and the thumbnail image beneath the protocol step.

At block 420, if the user adds measurements and annotations to the full size image, the system displays on the GUI a list of these with details in the measurement text box associated with the visual protocol. The four elements of a visual protocol (i.e., a check list, a scan map, a text box, and thumbnail gallery) are cross-referenced so that selecting an image/marker in one selects it on the other three, and displays the full size image as a working image.

Figure 5:
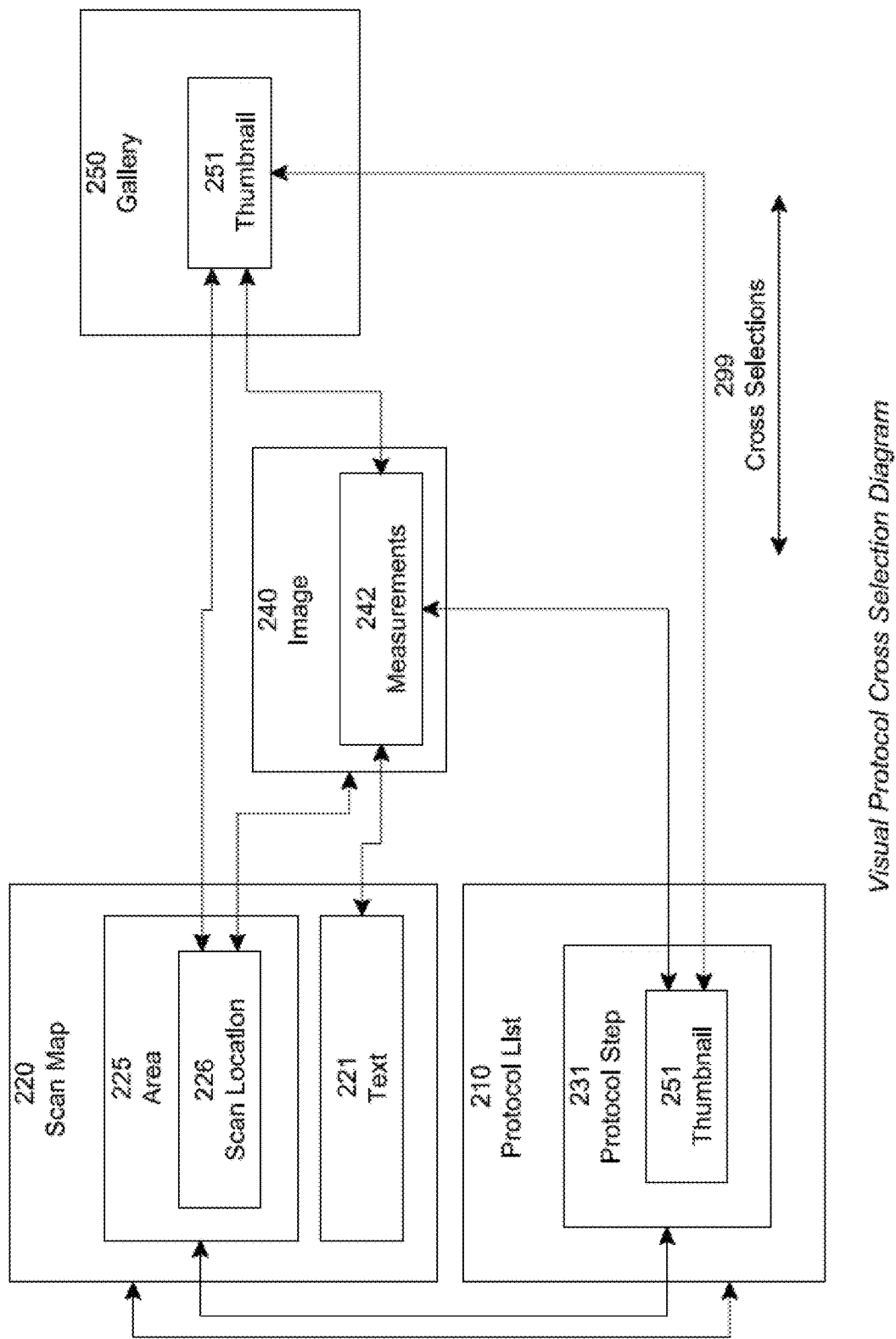
FIG. 5 is a functional flow diagram illustrating various flows and steps that can be done when performing the visual protocol, according to various embodiments.

The cross referencing (e.g., associating) of the protocol list 210, the scan map 220, the text box 221, and thumbnail gallery images 20 are further described in reference to FIG. 5, which illustrates a flow diagram showing various flows and steps that can be done when performing the visual protocol, according to various embodiments. Information relating to a scan map 220 (e.g., scan area 225, scan location 226 and text 221), a protocol list 210 (e.g., protocol steps 231, thumbnail image 251), a working image 240 (e.g., measurements 242), and a thumbnail gallery 250 (having one or more thumbnails 251) can be displayed on the interface 112 of the processing system 110. For example, as illustrated in the GUI shown in FIG. 3. The arrows in FIG. 5 represent a cross selection effect that the system employs when one of the items is selected by a user, for example, through a touch input on the interface 112. That is, when any of the items are selected, the associated items are also selected. For example, selecting a protocol list 210 automatically selects the associated scan map 220, and vice versa. Selecting a protocol step 231 automatically selects the associated area 225 in the scan map 220, and vice versa. Selecting a thumbnail 251 in the gallery automatically displays the associated image 240, selects and displays the protocol step it is associated with, selects the associated thumbnail 251 beneath its protocol step 231, and selects the associated scan location 226, in the associated area 225 of the scan map 220, and vice versa. Selecting a thumbnail 251 also automatically selects measurements 242 that are associated with thumbnail 251, and vice versa. Selecting text 221 related to a scan map automatically selects the associated measurements 242, and they can be automatically displayed on the associated image 240. Selection of a scan location 226 automatically selects the associated image 240, and it can display this image. As a visual protocol is completed, the system can save all the information related to the visual protocol, including patient information and associations to the related scan map, ultrasound images, measurements, and annotations of the visual protocol, in a completed visual protocol associated with a particular patient, which is referred to herein as a patient protocol 119 (FIG. 1). In some embodiments, the patient protocol 119 include a copy of the images and other information that is associated with the patient protocol 119. In other embodiments, the patient protocol 119 may include a link or another reference to the ultrasound images that were used to complete the patient protocol (e.g., in instances where the size and number of the ultrasound images prohibits copies of them to be included in the patient protocol due to storage restrictions). As mentioned above, the completed patient protocol 119 can then be provided to an output device 152 or to another system via a network link 128, and be used for further analysis of the patient.

Figure 6:
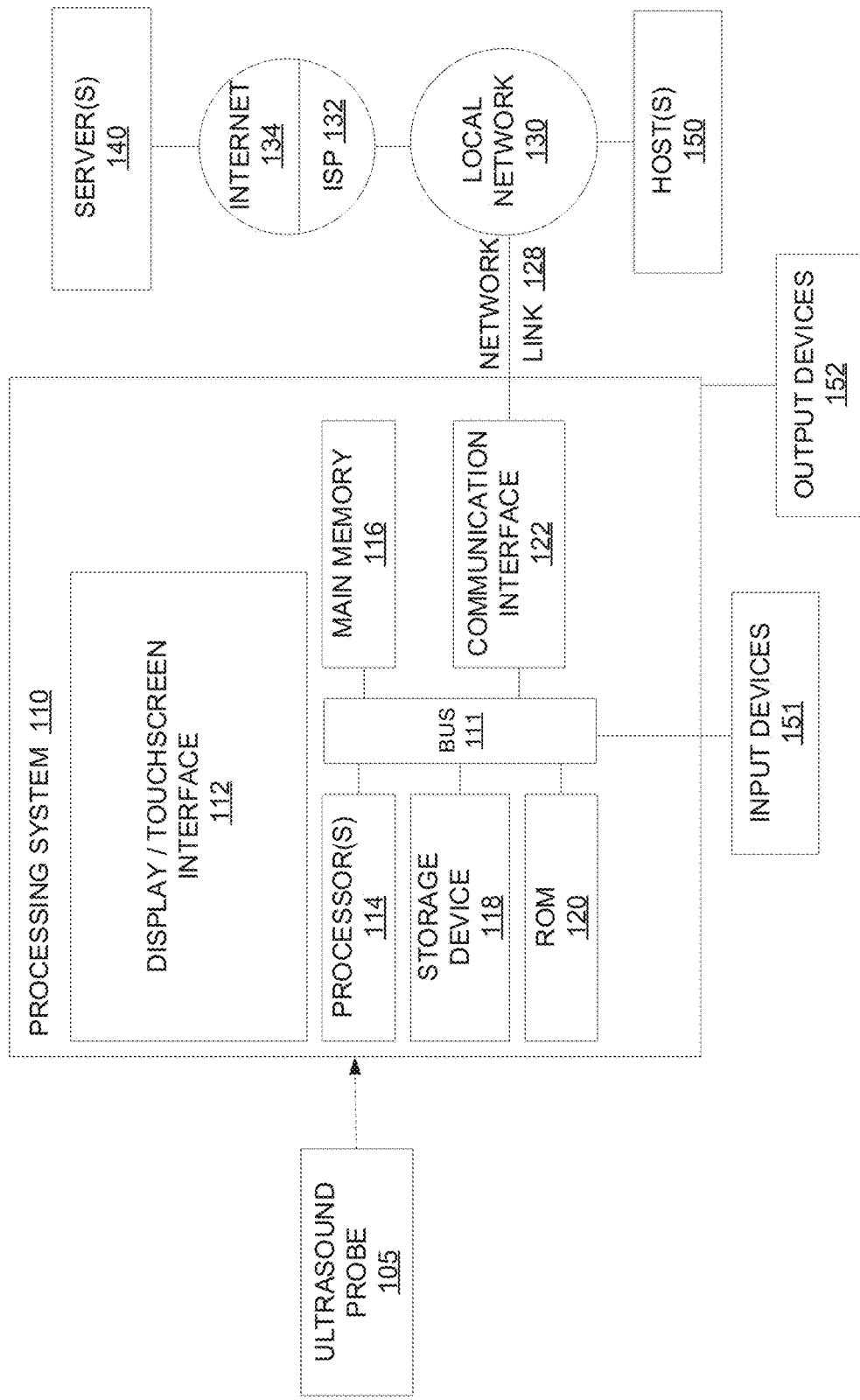
FIG. 6 is a block diagram illustrating an example of an ultrasound system that is adapted to perform functionality described herein.

FIG. 6 is a block diagram illustrating an example of an ultrasound system 10 that is adapted to perform functionality described herein. As illustrated in FIG. 1, the ultrasound system 10 includes an ultrasound probe 105 in communication with the processing system (computer system) 110. The ultrasound probe 105 can be connected to the computer system 110 via a wired or a wireless connection that allows the ultrasound probe 105 to provide ultrasound images to the computer system 110, and allows the ultrasound probe 105 to receive control signals from the computer system 110 the control signals indicating how ultrasound images should be collected.

The computer system 110 includes a bus 111 or other communication mechanism for communicating information, and a hardware processor (or multiple processors) 114 coupled with bus 111 for processing information. Hardware processor(s) 114 may be, for example, one or more general purpose microprocessors.

Computer system 110 also includes a main memory 116, such as a random access memory (RAM), cache and/or other dynamic storage devices, coupled to bus 111 for storing information and instructions to be executed by processor 114. Main memory 116 also may be used for storing temporary variables or other intermediate information during execution of instructions to be executed by processor 114. Such instructions, when stored in storage media accessible to processor 114, render computer system 110 into a special-purpose machine that is customized to perform the operations specified in the instructions. The main memory 116 may, for example, include instructions to allow a user detect and delineate graphical representations of features in ultrasound images, for example, as indicated in FIGS. 2-10.

Computer system 110 further includes a read only memory (ROM) 120 or other static storage device coupled to bus 111 for storing static information and instructions for processor 114. A storage device 118, such as a SSD drive, magnetic disk, optical disk, or USB thumb drive (Flash drive), etc., is provided and coupled to bus 111 for storing information and instructions.

Computer system 110 may be coupled via bus 111 to a display 112 (for example, a touch screen display) for displaying information to a computer user. One or more input devices 151 which may include alphanumeric and other keys and/or provide cursor control (e.g., mouse, trackball, or cursor direction keys) for communicating direction information and command selections to processor 114 and for controlling cursor movement on display 112 can be coupled to bus 111 for communicating information and command selections to processor 114.

Computer system 110 may include a user interface module to implement a GUI that may be stored in a mass storage device as computer executable program instructions that are executed by the computing device(s). Computer system 110 may further, as described below, implement the techniques described herein using customized hard-wired logic, one or more ASICs or FPGAs, firmware and/or program logic which in combination with the computer system causes or programs computer system 110 to be a special-purpose machine. According to one embodiment, the techniques herein are performed by computer system 110 in response to processor(s) 114 executing one or more sequences of one or more computer readable program instructions contained in main memory 116. Such instructions may be read into main memory 116 from another storage medium, such as storage device 118. Execution of the sequences of instructions contained in main memory 116 causes processor(s) 114 to perform the process steps described herein. In alternative embodiments, hard-wired circuitry may be used in place of or in combination with software instructions.

Various forms of computer readable storage media may be involved in carrying one or more sequences of one or more computer readable program instructions to processor 114 for execution. For example, the instructions may initially be carried on a magnetic disk or solid state drive of a remote computer. The remote computer can load the instructions into its dynamic memory and send the instructions over a network link 128. Bus 111 carries the data to main memory 116, from which processor 114 retrieves and executes the instructions. The instructions received by main memory 116 may optionally be stored on storage device 118 either before or after execution by processor 114.

Computer system 110 also includes a communication interface 122 coupled to bus 111. Communication interface 122 provides a two-way data communication coupling to the network link 128 that is connected to a local network 130. For example, communication interface 122 may be an integrated services digital network (ISDN) card, cable modem, satellite modem, or a modem to provide a data communication connection to a corresponding type of telephone line. As another example, communication interface 122 may be a local area network (LAN) card to provide a data communication connection to a compatible LAN (or WAN component to communicate with a WAN). Wireless links may also be implemented. In any such implementation, communication interface 122 sends and receives electrical, electromagnetic or optical signals that carry digital data streams representing various types of information.

Network link 128 typically provides data communication through one or more networks to other data devices. For example, network link 128 may provide a connection through local network 130 to a host computer 150 or to data equipment operated by an Internet Service Provider (ISP) 132. ISP 132 in turn provides data communication services through the world wide packet data communication network now commonly referred to as the "Internet" 134. Local network 130 and Internet 134 both use electrical, electromagnetic or optical signals that carry digital data streams. The signals through the various networks and the signals on network link 128 and through communication interface 122, which carry the digital data to and from computer system 110, are example forms of transmission media. Computer system 110 can send messages and receive data, including program code, through the network(s), network link 128 and communication interface 122. In the Internet example, a server 140 might transmit a requested code for an application program through Internet 134, ISP 132, local network 130, the network link 128, and communication interface 122. The received code may be executed by processor 114 as it is received, and/or stored in storage device 118, or other non-volatile storage for later execution.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Implementation Considerations

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple one. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

"Logic" refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter). Those skilled in the art will appreciate that logic may be distributed throughout one or more devices, and/or may be comprised of combinations of memory, media, processing circuits and controllers, other circuits, and so on. Therefore, in the interest of clarity and correctness logic may not always be distinctly illustrated in drawings of devices and systems, although it is inherently present therein.

The techniques and procedures described herein may be implemented via logic distributed in one or more computing devices. The particular distribution and choice of logic will vary according to implementation. Those having skill in the art will appreciate that there are various logic implementations by which processes and/or systems described herein can be effected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations may involve optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure.

In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory. In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuitry forming a communications device (e.g., a modem, communications switch, or optical-electrical equipment).

One or more aspects or features of the subject matter disclosed or claimed herein (e.g., processes and methods) may be realized in digital electronic circuitry, integrated circuitry, specially designed application specific integrated circuits (ASICs), field programmable gate arrays (FPGAs) computer hardware, firmware, software, and/or combinations thereof. These various aspects or features may include implementation in one or more computer programs that may be executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server may be remote from each other and may interact through a communication network. The relationship of client and server arises by virtue of computer programs running on the respective computers and having a client-server relationship to each other.

These computer programs, which may also be referred to as programs, software, software applications, applications, components, or code, may include machine instructions for a programmable controller, processor, microprocessor or other computing or computerized architecture, and may be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium. The machine-readable medium may alternatively or additionally store such machine instructions in a transient manner, such as for example as would a processor cache or other random access memory associated with one or more physical processor cores.

In some embodiments, to provide for interaction with a user, one or more aspects or features of the subject matter described herein may be implemented on a computer having a display device for displaying information to the user, and an input interface by which the user may provide input to the computer. Other kinds of devices may be used to provide for interaction with a user as well. Other possible input devices include touch screens or other touch-sensitive devices such as single or multi-point resistive or capacitive trackpads, voice recognition hardware and software, and the like.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Computer readable program instructions, may as also referred to herein as, for example, "code," "instructions," "module," "application," "software application," and/or the like. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device.

Aspects of the present disclosure are described herein with reference to methods, apparatus (systems), and computer program products according to embodiments of the disclosure. It will be understood that each method can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks. Any of the above-mentioned processors, and/or devices incorporating any of the above-mentioned processors, may be referred to herein as, for example, "computers," "computer devices," "computing devices," "hardware computing devices," "hardware processors," "processing units," and/or the like.

It will also be understood that, when a feature or element is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present. Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

The disclosed technology has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. An ultrasonic imaging system for performing ultrasound visual protocols, comprising:
   a computer hardware processor;
   a non-transitory computer storage medium, coupled to the computer hardware processor, storing instructions for the computer processor, on which an ultrasound visual protocol is stored, the visual protocol having protocol steps indicating images and information to be collected to perform the visual protocol, and on which a scan map comprising a graphical representation of anatomy being examined for the visual protocol is stored, the scan map associated with the visual protocol;

a display screen, coupled to the computer hardware processor and to the non-transitory computer storage medium, the instructions configuring the computer processor to cause presentation of a graphical user interface on the display screen configured to show the visual protocol and the associated scan map, and information associated with steps of the visual protocol is displayed on a first panel of the user display, an ultrasonic image of anatomy being examined with the selected visual protocol, and selectable thumbnail ultrasound images of the anatomy being examined, wherein the user interface is configured to receive for an object identified in an image, of object measurement information and object location information based on the selected visual protocol, and in response to receiving the object measurement and location information, to display location information of the object on the image and measurement information of the object in the first panel.

2. The ultrasonic imaging system of claim 1, wherein the graphical user interface is configured to display the ultrasonic image of anatomy being examined with the selected visual protocol in a second panel, and to display the selectable thumbnail ultrasound images of the anatomy being examined in a third panel.

3. The ultrasonic imaging system of claim 1, further comprising an ultrasound probe in communication with the computer hardware processor for acquiring ultrasonic images.

4. The ultrasonic imaging system of claim 1, wherein the user interface is further configured to receive a selection of an ultrasound visual protocol, and in response to display steps for the selected ultrasound visual protocol.

5. The ultrasonic imaging system of claim 4, wherein the user interface is further configured to receive a selection of a step of the selected ultrasound visual protocol, and in response to display a scan map associated with the selected step of the ultrasound visual protocol.

6. The ultrasonic imaging system of claim 5, wherein for a selected step, the user interface is further configured to receive a selection of an ultrasound image, and wherein the system is configured to associate the selected ultrasound image with the selected step, to save the image, and to add a thumbnail image of the selected ultrasound image on the user interface, the thumbnail image having an indicator showing it is the selected image.

7. The ultrasonic imaging system of claim 6, wherein the user interface is further configured to receive input to add a scanned position of the selected image to the scan map.

8. The ultrasonic imaging system of claim 1, wherein the user interface is further configured to display information needed to be determined based on the selected protocol, and to receive touch inputs to measure an object displayed on the working image, and wherein the system is configured to determine measurements of the object and display them in the first panel of the user interface.

9. The ultrasonic imaging system of claim 8, wherein determined measurements comprise the area of an object.

10. The ultrasonic imaging system of claim 8, wherein the determined measurements comprise the perimeter of an object.

11. A method of performing a visual ultrasound protocol, the method comprising:

generating and displaying on a touch-screen image display, a graphical user interface that to display information and receive input for performing a visual protocol, including displaying one or more visual protocols, in response to receiving an input selection of a visual protocol to perform, displaying steps of the visual protocol on the graphical user interface, for each step in the protocol, in response to receiving an input selection of a protocol step, automatically displaying an associated scan map, in response to receiving an input selection of a displayed image to save, generating thumbnail representation of the image and displaying the thumbnail representation in a panel on the graphical user interface for displaying the gallery of thumbnail image representations, displaying the thumbnail representation in the protocol step, associating the image with a scan location on the scan map, and displaying the scan location on the scan map, in response to receiving measurement information relating to the image, associating the measurement information with the image and the protocol step, in response to receiving annotation information relating to the image, associating the annotation information with the image and the protocol step, and storing the visual protocol such that the stored visual protocol includes associations to all of the images, measurements, and annotations related to each of the steps of the visual protocol, wherein the method is performed by one or more computer hardware processors executing computer-executable instructions on a non-transitory computer storage medium.

12. The method of claim 11, further comprising receiving the ultrasonic image of anatomy being examined from an ultrasound probe.

13. The method of claim 11, wherein one or more computer hardware processors are configured to execute the computer-executable instructions to further configure the user interface to receive a selection of a step of the visual protocol and receive a selection of an ultrasound image, and wherein the system is configured to associate the selected ultrasound image with the selected step, to save the image, and to add a thumbnail image of the selected ultrasound image on the user interface, the thumbnail image having an indicator showing it is the selected image.

14. The method of claim 11, wherein the wherein one or more computer hardware processors are configured to execute the computer-executable instructions to further configure the user interface to receive input to add a scanned position of the selected image to the scan map.

15. The method of claim 11, wherein the wherein one or more computer hardware processors are configured to execute the computer-executable instructions to further configure the user interface to receive touch inputs to measure an object displayed on the working image, wherein the system is configured to determine measurements of the object and display them in the user interface.

16. The method of claim 15, wherein determined measurements comprise the area of an object.

17. The method of claim 15, wherein determined measurements comprise the perimeter of an object.

18. An ultrasonic imaging system for performing visual protocols by displaying ultrasound images and corresponding visual protocols, including images rendered from the ultrasound image and measurements and location information of objects in the ultrasound images, the system comprising:
- a non-transitory computer storage medium storing computer-executable instructions,
  - an ultrasound visual protocol, the visual protocol having protocol steps indicating images and information to be collected to perform the visual protocol, and
  - a scan map associated with the visual protocol, the scan map comprising a graphical representation of anatomy being examined for the visual protocol;
- one or more computer hardware processors in communication with the non-transitory computer storage medium and configured to execute the computer-executable instructions to:
  - generate and display a user interface having a first panel including the visual protocol, the associated scan map, and information associated with steps of the visual protocol;
  - generate and display in the user interface a second panel including an ultrasonic image of anatomy being examined with the selected visual protocol;
  - generate and display in the user interface a third panel including selectable thumbnail ultrasound images of the anatomy being examined;
  - wherein the user interface is configured to receive, object measurement information and object location information for an object identified in an image, based on the selected visual protocol, and in response to receiving the object measurement and location information, to display location information of the object on the image in the second panel and measurement information of the object in the first panel.

19. The system of claim 18, further comprising an ultrasonic probe in communication with the one or more computer hardware processors to receive an image of anatomy being examined from the ultrasound probe.

* * * * *